United States Patent [19]

Freeland

[11] Patent Number: 5,211,169
[45] Date of Patent: May 18, 1993

[54] BLOOD POOL IMAGING AND ANALYSIS TECHNIQUE USING ULTRASOUND

[75] Inventor: John C. Freeland, Boulder, Colo.

[73] Assignee: Prism Imaging, Inc., Broomfield, Colo.

[21] Appl. No.: 613,318

[22] Filed: Nov. 8, 1990

[51] Int. Cl.$^5$ .............................................. A61B 8/00
[52] U.S. Cl. ........................... 128/661.08; 128/661.10
[58] Field of Search ...................... 128/661.07, 661.08, 128/661.09, 661.10, 661.04, 916

[56] References Cited

U.S. PATENT DOCUMENTS

| | | | |
|---|---|---|---|
| 4,095,597 | 6/1978 | Hassler | 128/661.10 |
| 4,257,278 | 3/1981 | Papadofrangakis et al. | 128/661.10 |
| 4,785,402 | 11/1988 | Matsuo et al. | 128/661.08 |
| 4,858,614 | 8/1989 | Stevens et al. | 128/661.07 |
| 4,873,985 | 10/1989 | Nakajima | 128/661.10 |
| 4,896,674 | 1/1990 | Seo | 128/661.09 |
| 4,966,150 | 10/1990 | Etienne et al. | 128/661.04 |

OTHER PUBLICATIONS

Bjorn A. J. Angelsen, "On the Design of 2D Flow Imaging Systems," Feb. 1986.
Joan S. Weszka, "Survey: A Survey of Threshold Selection Techniques," *Computer Graphics and Image Processing*, No. 7, p. 259 (1978).
E. Garcia, P. Gueret, M. Bennett, E. Corday, W. Zwehl, S. Meerbaum, S. Corday, H. J. C. Swan, D. Berman, "Real Time Computerization of Two-Dimensional Echocardiography," *American Heart Journal*, vol. 101, No. 6, p. 783 (Jun. 1981).
E. Garcia, A. Ezekial, R. Levy, W. Zwehl, K. Ong. E. Corday, J. Areeda, S. Meerbaum, S. Corday, "Automated Computer Enhancement and Analysis of Left Ventricular Two Dimensional Echocardiograms," *IEEE Computer Society: Computers in Cardiology*, p. 399 (1982).
C. A. McNary and D. J. Skorton, "Segmentation-Based Boundary Extraction for Endocardial Definition in Cross-Sectional Echocardiography", *Pattern Recognition Theory and Applications*, p. 465 (1982).
Fourth Annual Symposium, "Recent Advances in Doppler Color Flow Mapping", Echocardiographic Laboratory, University of Alabama Hospital, University of Alabama-Birmingham, Mar. 25–26, 1988.

*Primary Examiner*—Francis Jaworski
*Assistant Examiner*—George Manuel
*Attorney, Agent, or Firm*—Holland & Hart

[57] ABSTRACT

A blood pool imaging and analysis technique and apparatus uses ultrasound to examine areas of interest within the human body. The Doppler effect is used to determine the velocity of blood and tissue movement. Color flow imaging is used to display the moving blood pools and tissue by representing movement toward the transducer as one color, movement away from the transducer as a second color and movement which is outside of the sampling limits as a third color. Since the blood pool movement generally exceeds the rate at which the heart or organ walls move in creating the blood movement, the sampling limits can be adjusted so that the blood pool movement is outside of the limits. The resulting image of the blood pool movement, in the third color, can be used to calculate heart function parameters such as the ejection fraction.

22 Claims, 3 Drawing Sheets

Fig_1

Fig_2
PRIOR ART

Fig_4

Fig_3

Fig_5

BLOOD POOL IMAGING AND ANALYSIS TECHNIQUE USING ULTRASOUND

This invention relates to the use of ultrasound for medical purposes, and more particularly, to a noninvasive diagnostic technique using ultrasound to image moving pools of blood in internal organs of the body to evaluate the function of such organs, especially the human heart.

BACKGROUND OF THE INVENTION

The human heart is made up of four chambers: the left and right atria and the left and right ventricles. Simply put, the right atrium receives blood from the veins of the body and the right ventricle pumps this blood through the pulmonary arteries to the lungs. The left atrium receives blood from the lungs through the pulmonary veins and the left ventricle pumps this blood through the aorta systemically to the tissues of the body.

The left ventricle (LV) is commonly analyzed by physicians in order to determine the presence of coronary circulatory problems in a patient. Coronary artery disease can be diagnosed through observation of the functioning of the left ventricle. Roughly eighty percent of all heart disease is coronary artery disease.

While as many as three hundred different parameters regarding heart functioning are known to exist, the most common and widely used parameter for evaluating the LV function is the ejection fraction. The ejection fraction (EF) is the percentage of blood ejected or displaced from the LV with each contraction. A fully contracted ventricle is in what is known as the systolic state, while a fully dilated ventricle is in the diastolic state. Therefore, the EF equals the difference in blood volume in the LV between the systolic and diastolic states divided by the blood volume in the LV in the diastolic state. Thus, $$EF = \frac{V_D - V_S}{V_D} \times 100$$

where
EF is expressed as a percentage
$V_D$=blood volume in LV in diastolic state
$V_S$=blood volume in LV in systolic state.

An EF in the range of fifty to sixty percent can be expected from a normal, healthy heart. An EF in the range of thirty to forty percent is a sign of improper functioning, while an EF of twenty percent is accompanied by serious consequences.

LV functioning has been observed by ultrasound detection of the heart wall, known as the endocardium. However, the observation of the dilation and contraction of the LV is an indirect method of measuring the ejection fraction, since the EF is a percentage of blood ejected. This indirect method is inaccurate because of poorly defined endocardiums, ventricular hypertrophy and misshapen cardiac chambers, i.e. aneurysms. Therefore, to accurately analyze LV functioning the volume of blood must be measured directly.

The field of nuclear imaging or nuclear medicine has been used to image a blood pool in the LV. Nuclear imaging is an invasive diagnostic technique which requires an injection of a radioactive isotope into the blood stream. This radioactive isotope is normally tagged or attached to a pharmaceutical drug before injection into the patient's blood stream. The isotope radiates nuclear energy which can be detected by a sensor, commonly known as a gamma camera, pointed at the area of interest, in this case the LV. When averaged over up to one thousand heart cycles or over twenty minutes, this nuclear imaging technique can produce an image of the blood pool in the LV both in the systolic and diastolic states. These images can either be manually analyzed to determine the EF and other LV functional parameters, or the images can be automatically analyzed by an image processor.

To analyze a "black-and-white" image with an image processor, the image is divided into an array of rows and columns of hundreds of picture elements, or pixels. Each pixel is assigned a value representing the "shade of gray" in that pixel. These values can then be analyzed by the image processing computer, with the use of known pattern recognition algorithms, to determine the boundaries of the blood pool in the LV. Once the boundaries are determined, known estimation algorithms are utilized to estimate the three-dimensional volume of the blood pool from the two-dimensional image of the blood pool. The EF and other LV functional parameters can then be calculated.

There are several drawbacks to nuclear imaging to determine LV function. The most serious is the invasive nature of injecting a radioactive isotope tagged to a pharmaceutical drug into the blood stream. The technique is also inaccurate due to the need to average the image over a twenty minute period. During this period the patient may move or the heart cycle or rate may speed up or slow down. Either of these two changes will cause inaccuracies in the image.

A second invasive diagnostic technique involves the use of a catheter to inject a dye into the bloodstream near the heart. This dye is selected to be absorbent to x-ray energy. Standard x-ray techniques are then used to image the blood pool in the LV by transmitting x-ray energy through the LV from one side of the body while detecting x-ray energy on the other side of the body. The dye in the LV absorbs the x-ray energy and creates a shadow in the image which can thereafter be evaluated. Again, this invasive method has the disadvantage of injecting a foreign substance into the blood stream. Furthermore, x-ray techniques work best for still images and not dynamic or moving images.

In addition to the use of ultrasound to observe a moving wall of the heart, ultrasound has been used to observe or measure the flow of blood. By definition, ultrasound is a sound pressure wave having a frequency greater than twenty kilohertz. Most ultrasound sensors utilize the Doppler effect to sense motion. In simple terms, the Doppler effect is the frequency shift resulting from the reflection of a constant frequency signal off of a moving object. An object moving toward the signal will reflect a higher frequency signal. Conversely, an object moving away from the signal will reflect a lower frequency signal. The magnitude of the frequency shift is proportional to the speed of the moving object. Stationary objects will not change the frequency of the reflected signal.

In the case of monitoring blood flow with ultrasound, the moving objects are the red blood cells in the bloodstream. An ultrasound transducer, for converting an electrical signal to transmitted ultrasound and for converting received ultrasound to an electrical signal, is placed over the area of interest in a patient's body. This area of interest for observation of LV functioning with ultrasound is the bottom or apex of the heart. A two-dimensional image is generated by sweeping the transmitted direction of the ultrasound through a fixed angle, resulting in a wedge or sector shaped image.

It is common to use color video to represent the image received by the ultrasound sensor. The movement of blood toward the transducer (a positive Doppler frequency shift) has commonly been represented by red, an arbitrarily selected but universally applied color. The movement of blood away from the transducer (a negative Doppler frequency shift) has commonly been represented by blue, another arbitrarily selected color. Slow moving or stationary objects, including blood, are represented by grey. Greater rates of movement are represented by saturated shades (more white), and slower rates of movement are represented by less saturated shades (less white). Hence, such color ultrasound systems are known as color flow imaging systems.

One of the important aspects of color flow imaging involves sampling theory. Sampling theory reveals that the accuracy of the Doppler frequency shift determination is proportional to the time spent observing or measuring the movement of the object creating the shift. Since, as mentioned previously, the magnitude of the frequency shift is proportional to the speed of the moving object, slow moving objects will have small frequency shifts. Therefore, relatively more samples will be needed to accurately determine the speed of slow and stationary objects. The dynamics of the heart are such that the endocardium of the heart moves at a velocity which is believed to be in the range of ten centimeters per second (with some variation depending on exercise level and physical condition), while blood flow is at a velocity in the range of thirty to one hundred twenty centimeters per second. Flow rates near ninety centimeters per second typify leaks from valves and holes in vessels and chambers of the heart.

The color flow imaging systems can be optimized to look for velocities of a particular magnitude. When a moving object with a velocity outside of the limits of a selected range is encountered, there will exist an uncertainty as to the measurements of this out-of-limit velocity due to sampling theory limitations. When this occurs the movement is portrayed by a green color mixed with either red or blue, as appropriate. The green color was arbitrarily selected, and although not universal has become somewhat of a standard in the industry. Increasing degrees of uncertainty cause increasing amounts of the red or blue colors to be replaced with green. Adding the green to red obtains shades of yellow, and adding the green to blue obtains shades of cyan.

Since color flow imaging systems have primarily been used to detect leaks and defects or to measure the speed of blood flow, the velocity range is normally set to a maximum setting for observation of LV functioning, e.g. from thirty to one hundred twenty centimeters per second. This setting is then adjusted in an effort to reduce the amount of green in the object of interest. Such common usage has, however, not resulted in a significant capability to evaluate LV function including EF and other heart functional characteristics involving the movement of blood pools.

It is with respect to these and other considerations that the present invention has evolved.

SUMMARY OF THE INVENTION

The present invention uses ultrasound as a noninvasive diagnostic technique for imaging moving blood pools in the heart or another organ, by adjusting the movement velocity limits of the ultrasound apparatus to a minimum setting so that the moving organ or endocardium is within the desired limits and the faster moving blood pool is out-of-limits. This adjustment causes the blood pool, which is moving at a much greater and out-of-limit rate, to be displayed as a different color (primarily green) than the organ or endocardium. The resulting blood pool image is distinguishable from the remainder of the image by its out-of-limit color and can be analyzed to determine the size of the blood pool movement and other functional aspects of the organ or heart, including the ejection fraction.

The present invention has the advantage of providing an image of blood pools in the heart without injecting foreign agents into the bloodstream. The present invention transmits ultrasonic vibrations into the body as opposed to x-rays, dyes, radioactive isotopes and pharmaceutical drugs. In addition, the present invention achieves an accuracy level better than or comparable to previous methods in much less time than with previous methods. Furthermore, the present invention can automatically and directly calculate organ or heart functional parameters from a measurement of the blood pool rather than a measurement of the sizes of chambers of the heart or organs containing the blood pool.

According to a preferred aspect of the present invention, a series of pulses of ultrasonic signals of a predetermined frequency are transmitted into a patient's body and reflected off of the moving fluid and tissues in the patient's body. The reflected signals are used to calculate the range, position and velocity of the fluid and tissues. The velocity is calculated by use of the Doppler effect. The movement of the fluid and tissues in the area of interest can then be categorized by velocity, thus defining regions of distinct velocity. These regions can then be displayed as a color video image with distinct colors for distinct velocities.

A more complete understanding of the nature of the present invention and its advantages and improvements can be obtained from the following detailed description of a presently preferred embodiment of the invention taken in conjunction with the accompanying drawings, briefly described below, and from the appended claims.

DETAILED DESCRIPTION OF THE PREFERRED EMBODIMENT

Figure 1:
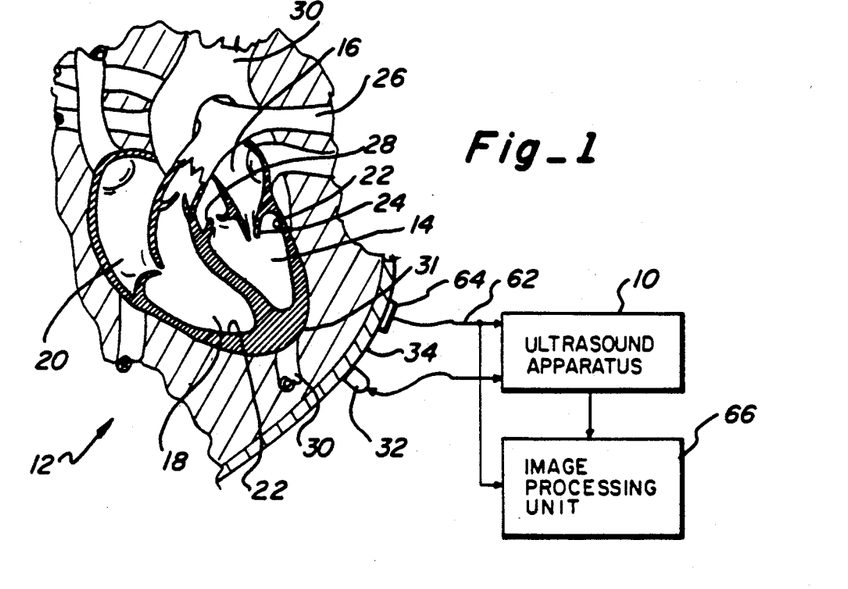
FIG. 1 is a generalized illustration of an ultrasound apparatus and an image processing unit according to the present invention by which ultrasound image information is obtained from a patient to evaluate the function of the patient's heart, which is also illustrated.

Referring to the drawings and specifically to FIG. 1, the present invention involves the use of an echocardiographic or ultrasound apparatus 10 for determining the performance of an individual's heart 12. As will be discussed more completely below, one of the major functions of the present invention is to evaluate the blood flow movement within the various chambers of the heart, which include the left ventricle (LV) 14, the left atrium 16, the right ventricle 18 and the right atrium 20, all of which are defined by the muscle wall or endocardium 22 of the heart 12. By observing blood flow movement within the heart chambers, various heart functions may be evaluated.

As previously mentioned, one of the most prevalent indices used for evaluation of heart function is the ejection fraction. Determining the ejection fraction (EF) takes into account the general condition of the left ventricle 14 or effectiveness of the endocardium 22 in forcing the blood from the LV. The EF is used to represent the heart's functional condition in a single number.

The present invention offers significant advantages and improvements in using ultrasound imaging to evaluate the left ventricle ejection fraction and many other heart functions involving blood flow and movement. In general the noninvasive imaging technique of the present invention involves considerably less risk to the patient than previous nuclear imaging and invasive catheterization techniques, while offering comparable or better analysis results of heart performance.

Figure 2:
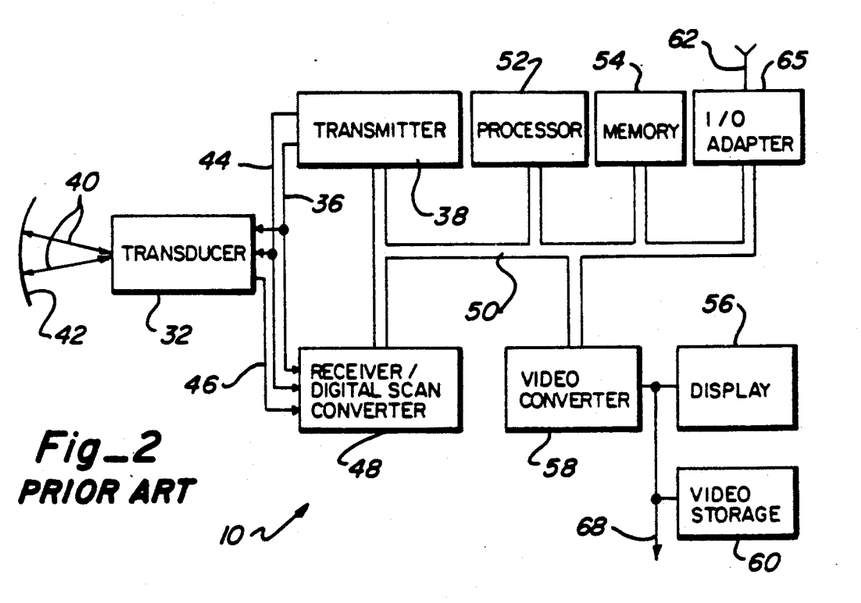
FIG. 2 is a block diagram of a prior art ultrasound apparatus, such as that shown in FIG. 1.

The typical ultrasound apparatus 10, which is also shown in generalized form in FIG. 2, can be used in practicing the present invention under the circumstances explained below. In general the ultrasound apparatus 10 includes a transducer 32 which is positioned on the skin 34 of a patient. The transducer 32 transmits ultrasound pulses in response to the application of electrical pulse signals 36 from a transmitter 38. The transmitted ultrasound pulses project into the patient's body where they encounter various structures, tissues, components and particles that cause a reflection or "echo" of the projected ultrasound pulses back to the transducer 32. The reflection itself induces changes in the ultrasound echo compared to the transmitted ultrasound pulses, and the echo ultrasound signals contain information regarding the location and movement of the structures, tissues, components and particles which cause the echo. The transmitted pulses and the received echo ultrasound signals form a beam 40 which scans through an angular sector 42 in a plane. The scanning effect is achieved by a scan signal 44 which is also transmitted from the transmitter in synchronism with the pulse signal 36. The scan signal causes either a mechanical movement of the transducer 32 or an electrical deflection of the transmitted pulses from the transducer.

The ultrasound echo is received by the transducer 32, and the transducer converts the echo into an electrical echo signal 46. The echo signals 46 are applied to a receiver and digital scan converter 48. The receiver and converter 48 utilizes the information from the echo signal, the pulse signal 36 and the scan signal 44 to develop the ultrasound image information which will be presented, usually in enhanced form by the ultrasound apparatus 10. The relative timing relationship of the pulse and echo signals are employed to develop range or distance information by which to obtain information only from a selected range of interest or location in the patient's body. The frequency difference between the ultrasound frequency of the transmitted pulses and the received echo signals is determinative of the rate of movement of a particle or structure which caused the reflection, in accordance with the well known Doppler theory. Position information representative of the location of the object causing the reflection is also developed by use of the scan signal 44. The position information is initially developed in a polar coordinate, two dimensional form due to the direct relationship of the range and velocity information relative to the angular sector 42. The position, velocity and range information constitute image information over the angular sector 42.

The digital scan converter aspect of the unit 48 converts the image information into digital scan signals which are supplied on a bus 50. The digital scan signals are obtained in incremental time segments and are typically assigned to sequential locations in a memory 54 of a computer formed by a processor 52 and the memory 54.

Much of the signal processing necessary to obtain the range, velocity and position information contained in the image information may be obtained from the inherent functionality of the receiver of the unit 48. However, some of or all of this signal processing capability may be accomplished by a computer formed by a processor 52 and a memory 54 which are also connected to the bus 50. The image, range, velocity and position information available from the receiver and converter 48 is stored in the system memory.

With many modern ultrasound apparatus, the image information may also be subjected to certain well known image enhancing operations in which the computer subjects the image information to image enhancing algorithms in order to obtain a more useful display of actual conditions free from some of the spurious effects which are inherent in ultrasound imaging. A variety of known algorithms are used to determine from the signals recorded in memory, the edges and other characteristic features represented by the data. These algorithms are known by various titles, and are readily available for use by those skilled in this field. In any event, the computer typically utilizes such algorithms under software control to derive the enhanced images. Usually the image information will be enhanced before it is recorded permanently in memory.

A display 56 visually presents the image information to the user. Typically the display will be a CRT or raster scan device, and the user may manually select a variety of information to be displayed. The information to be displayed is selected from the memory 54, and it is supplied to a video converter 58 which is also connected to the bus 50. The video converter 58 converts the information from digital form to an analog video format form and supplies it to the display 56. The video converter may supply the analog video signals in one of a variety of different known video formats. In addition, the analog video signals representative of the image information may also be stored in a video storage device or recorder 60, for subsequent analysis or use.

The transmitter 38 is also connected to the bus 50 and can also be controlled by the computer, if desired, when generating the pulse and scan signals 36 and 44, respectively. The pulse and scan signals are generated continuously and are not synchronized to the patient's heart function. However, for echocardiographic applications it is desirable to synchronize or trigger the storing of the image information relative to the heartbeat of the patient, and for this purpose a conventional electrocardiograph (EKG) signal 62 is supplied from an electrode 64 attached to the patient (FIG. 1). The EKG signal 62 is supplied to the bus 50 through a conventional I/O adapter 65. The signal 62 represents the electrical signal conducted to the nerves of the heart in order to cause the muscles to contract and beat. Typically the pulses forming each angular scan will be triggered relative to the R or major wave portion of the EKG signal 62. Occasionally, there are periods of arrythmia or variation from the normal rhythm of the heart. The processor is able to detect this arrythmia from the EKG signal 62 and not store or analyze images during such periods, or otherwise mark or note that the data for those images is subject to discrepancies.

By triggering the storing of image information at predetermined time intervals during each heart beat, frames or still images of the heart in a number of conditions are obtained. For example, if ten frames are obtained during each heartbeat, ten image frames will represent in still motion the condition of the heart during a single beat. Obtaining multiple frames of image information in this manner allows the frames to be separately examined and analyzed. Each frame is constituted of the composite of all of the digital signals recorded in memory 54 derived from the scan.

While the functionality and information available from an ultrasound apparatus 10 are well known and conventional, certain of these functions which are of importance to the present invention will be briefly described below.

The ultrasound apparatus has the capability of establishing a particular range or depth or region of interest within the interior of the patient's body over which signals will be developed to provide an image of the region of interest. This region of interest is determined by correlating and considering only those signals received within a predetermined range of time delays after the transmission signal is delivered. The signals developed in this region of interest relate to the physical location or position within the patient's body.

Another function available from the ultrasound apparatus is the ability to determine movement or flow. The movement or flow is created when a body or particle which the ultrasound strikes is moving either toward or away from the probe 32. The well known Doppler effect occurs, which results in a change in frequency of the reflected or echo signal. The degree to which the frequency is changed is representative of the rate of movement. Movement toward the transducer or away from the transducer is determined by the change in frequency of the received signal relative to the transmitted signal.

A further well known function of the ultrasound apparatus is the ability to select a limit or range of movements or flows to which the ultrasound apparatus will be primarily responsive. A typical range of movements from approximately six centimeters per second up to as great as one hundred twenty centimeters per second can be selected. Selection of the range of flows or movements result in changing the rate of sampling or transmission pulse delivery rate. When movements in the relatively high range are desired, a slower sampling rate is used, because more adequate information will be obtained as a result of the high rate of movement of the target and the relatively low sampling rate. On the other hand, when the relatively slow movements or flows are to be measured, a higher sampling rate must be selected. The rate of sampling relative to the desired range of movements or flows are related to one another by conventional sampling theory, generally referred to as the Nyquist limit. Nyquist theory relates to the rate of sampling relative to the rate of movement of a target in order to obtain full information relative to the movement of the target. In most conventional ultrasound apparatus, the range of movements or the Nyquist limit is generally variable from approximately as low as 8 centimeters per second, to as high as 100 centimeters per second.

Still another function of conventional ultrasound apparatus is to assign color to the display of information relative to the movements or flows. This is sometimes referred to as "color flow". For example, a target which moves at a particular rate toward the transducer is conventionally assigned a red color, while a target which moves away from the probe is assigned a blue color. The brightness of the red and blue color is intended to represent the amount or rate of movement. Brightness is controlled by mixing white with the red or the blue. A very saturated red color has a significant white component and represents a rapid movement toward the probe, and a very saturated blue also has a significant white component and represents a rapid movement away from the transducer. Slow or moderate movement toward the probe and slow or moderate movement away from the probe will result in relatively less saturated shades of red and blue, respectively, in which there is a lower amount of white. Accordingly, by the assignment of the colors, the operator not only obtains information regarding the structure and position due to the depth or region of interest adjustment, but also obtains information regarding the movement of that structure or target toward or away from the transducer by the color and information regarding the rate of movement by the brightness of the color.

Of course, not all of the particles which the ultrasound beam intercepts will move within the desired range of flows or movement. Those which are in excess of the upper limit of the range create additional signal effects. These additional signal effects are referred to herein as out-of-limit responses, and are typically referred to in conventional ultrasound terminology as aliasing, variance and phase shift. In general, aliasing relates to the degree to which a received signal exceeds the upper limit of the desired selected range of movement velocity. In general, variance relates to the degree to which all signals vary with respect to one another. Phase shifts relate to reflections of the signals in such a way that the signal itself is shifted beyond predetermined limits of acceptable time phase variation. In general, these out-of-limit responses relate to effects resulting from the reflection of ultrasound signals from movements beyond those within the selected range of movements. The out-of-limit response in general terms relates to the validity of the information obtained in the selected range of movements.

Of course, since not all of the signals are reflected at the selected range of movement or flow, due to the dynamic characteristics of many particles and structures within the human body, color has also been assigned to represent the gross extent of the out-of-limit response characteristics or uncertainty, in most conventional ultrasound apparatus. In general, the manner in which aliasing, variance and phase shifts are combined to obtain a single representation of the out-of-limit response characteristics are to a large measure proprietary in most conventional ultrasound machines, but nonetheless, such representations are available on the vast majority of conventional ultrasound machines. This quantity of out-of-limit response is assigned a color which is displayed in conjunction with the red and blue colors representative of the desired movement toward and away from the transducer, represented by the red and blue. Usually the color green is assigned to represent the extent of out-of-limit response. In addition, the saturation level of green is also changed to represent the magnitude of the out-of-limit response. In most conventional ultrasound machines the green is then combined with the red and blue colors to provide a further visual indication of the extent to which the measured range of movement or flow is subject to out-of-limit response or validity. Adding the green to red obtains shades of yellow, and adding the green to blue obtains shades of cyan.

Thus, from the foregoing information, the ultrasound apparatus 10 creates a display at 56 of the internal structure within a particular depth or range of interest, an indication of a rate of movement within a preselected velocity range within that range of interest, and an indication of the validity of that velocity, all on the single display, by use of the display characteristics known as color flow imaging.

Figure 3:
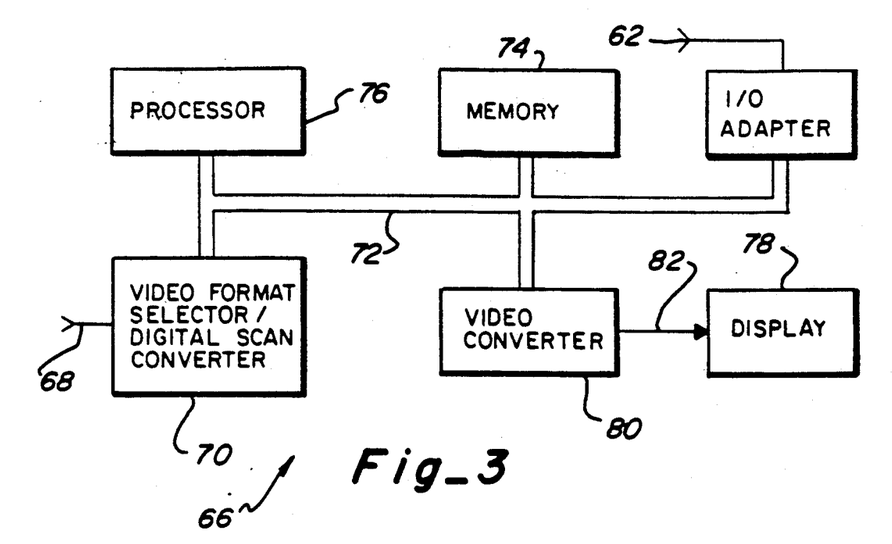
FIG. 3 is a block diagram of an image processing unit, shown in FIG. 1.

The present invention may be practiced by using a conventional ultrasound machine 10, such as the ACCUSON 128 machine, with modifications primarily in software to achieve the additional functionality described below. Alternatively the invention may be practiced by connecting a separate image processing unit 66 to the ultrasound apparatus 10 as is shown in FIG. 1 The image processing unit 66 is shown in FIG. 3 and it will be connected so as to receive a video display signal at 68 from the ultrasound apparatus 10 as shown in FIG. 2 to obtain the signals supplied to the display 56. By accessing the computer memory 54, the image processing unit has the ability to use the stored image information in order to process it in accordance with the present invention. As will be appreciated from the following description, the image processing unit 66 is essentially duplicative of the inherent functional capability of a conventional ultrasound apparatus 10. Thus, the present invention may also be practiced by providing additional software functionality within a conventional ultrasound apparatus.

Details regarding the conventional components of the image processing unit 66 are shown in FIG. 3. The video display signal 68 is initially applied to a video format selector and digital scan converter 70. The video format selector of the unit 70 converts the video format of the video display signal 68 supplied by the ultrasound apparatus to an appropriate video format for image processing. This video display signal 68 is commonly in one of three standard video formats, NTSC, SVHS or RGB. The video format selector of the unit 70 converts the standard video format into a standard component video format such as YUV, RGB, R-Y B-Y, or HSI. The digital scan converter of the unit 70 converts the standard component video format into digital form and applies it to a bus 72. The digital signals may be read into a memory 74 where they may thereafter by acted on by a processor 76 operating under the control of software recorded in the memory 74 to achieve the functionality of the present invention. The processor 76 and the memory 74 form an image processing unit computer which may be used to practice the present invention. The generalized diagram of the memory 74 (as is the memory 54 of the ultrasound apparatus 10, FIG. 2) is intended to represent all types of memory, such as main processor memory, scratch pad memory, RAM and the like necessary to contain the software and data for the processor 76 to achieve the processing functions described herein. As discussed previously in conjunction with FIG. 2, an EKG signal 62 may be supplied to the bus 72 through a conventional I/O adapter 77.

A display 78 is available to present the image information obtained. The image information may be obtained from the memory 74, or from information obtained from the processor 76 or from information obtained directly from the selector and converter 70 over the bus 72. In all cases, however, a video converter 80 converts the digital data into a video signal 82 which drives the display 78.

Figure 4:
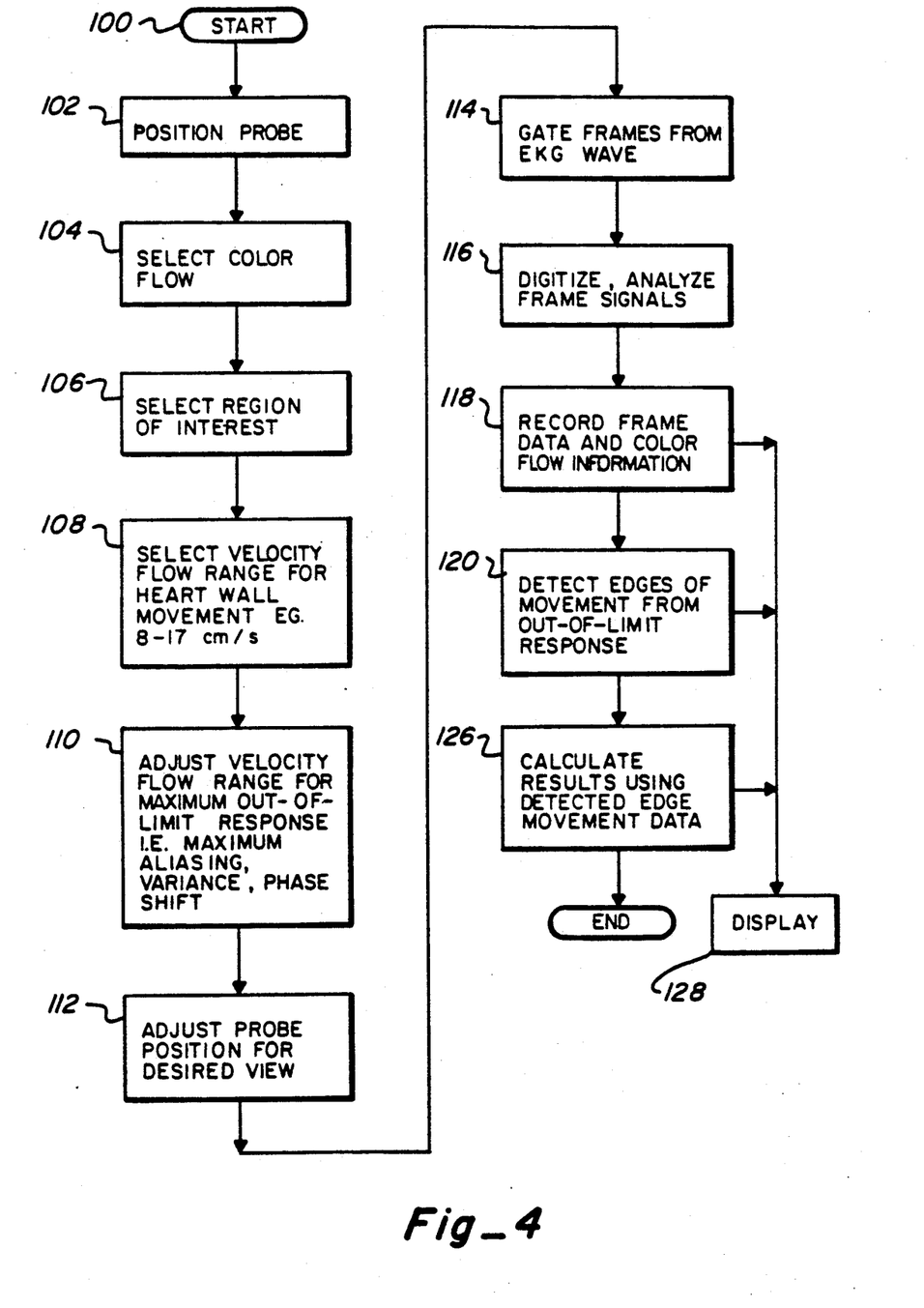
FIG. 4 is a flow diagram illustrating the practice of the present invention in conjunction with an image processing unit and/or an ultrasound apparatus, shown in FIGS. 1, 2 and 3.

The practice of the present invention for determining heart function, and for determining left ventricle function and particularly for determining left ventricle ejection fraction is illustrated by the flow chart shown in FIG. 4. Many of the steps illustrated in the flow chart shown in FIG. 4 utilize the conventional ultrasound techniques and functionality previously described in conjunction with FIGS. 1 to 3, and hence will be only briefly described in conjunction with FIG. 4. Steps involved in practicing the preferred embodiment are described and shown with the aid of reference numbers in FIG. 4.

The functionality starts (100), and the first step thereafter is to position the probe (102) in order to observe a desired part of the patient. Thereafter, color flow is selected (104) by the operator manually selecting this functionality from the ultrasound apparatus. In addition, the operator manually selects the depth or region of interest (106) over which the ultrasound signals will be effective. Further, the operator selects the velocity flow range (108). When the present invention is used for determining the left ventricle ejection fraction or other characteristics having to do with blood pool movement within the heart, the velocity range selected is preferably within the same range of velocity as movement of the endocardium muscle, for example, within the range of 8 to 17 centimeters per second Next, a very important step of the present invention which differentiates the present invention from conventional ultrasound practice is adjusting the velocity flow range for maximum out-of-limit response (110). In many regards, the steps 108 and 110 involve setting the Nyquist sampling limit on a conventional ultrasound apparatus. As noted previously, out-of-limit response relates to obtaining a maximum of aliasing, variance and phase shift. In conventional terms, this involves tuning the ultrasound apparatus to obtain the greatest amount of green color influence over the red color and blue colors normally presented in most conventional ultrasound displays. As will be appreciated, by creating the maximum out-of-limit response, a color area will be derived in which maximum blood flow or movement will be revealed. This maximum blood flow movement will not necessarily be the same as that volume encased within the endocardium muscle which defines a chamber or area, for example the left ventricle, because despite movement of the endocardium muscle, the blood itself may not move significantly throughout the whole chamber, but instead will only move in a reduced or diminished sized pool. By obtaining the maximum out-of-limit response, the flow rates within that pool will be considerably higher than the adjusted velocity flow range (step 110), and therefore will achieve maximum out-of-limit response. Blood areas within the chamber which do not move rapidly but instead move only with the contracting and expanding wall of the heart, will be within the adjusted velocity flow range (step 110) and there will appear only as conventional red and blue colors.

Implementation of the present invention in a specific, non-conventional ultrasound apparatus may not require the apparatus to specifically provide aliasing, variance and phase shift information. Instead, the apparatus can simply determine one or more of these out-of-limit conditions relative to the selected limit and attribute to the out-of-limit condition(s), a specific coloring or designation in the image.

Figure 5:
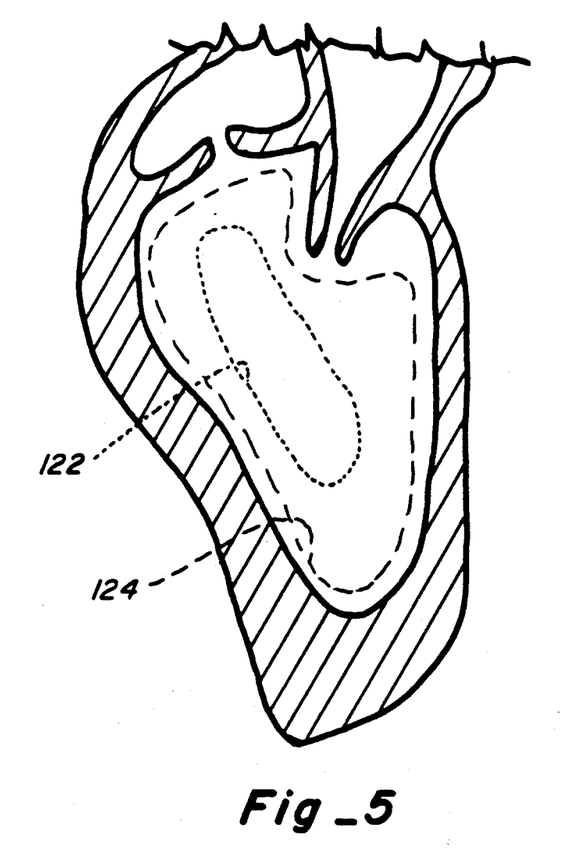
FIG. 5 is a generalized illustration of the left ventricle of the heart shown in FIG. 1, with an area bounded by shorter dash lines representing blood pool movement during systolic conditions, with an area bounded by longer dash lines representing blood pool movement during diastolic conditions, and with the area between the shorter and longer dash lines representing the amount of fluid ejected from the left ventricle during a heartbeat.

As will be seen from FIG. 5, actual heart performance is determined by the blood pool which experiences considerable movement, as will be revealed by the color associated with the out-of-limit response.

Thereafter, the probe is adjusted (112) to obtain the desired view, as shown in FIG. 4. For example, there are a number of different views which are recognized for measuring heart function, the most common being the two and the four chamber views. One of the most common views requires the transducer 56 to be positioned at the apex 31 of the heart as is shown in FIG. 1. Thereafter the probe can be rotated to provide the desired axis or viewing plane through the heart to obtain the desired information. Another common view which can be used is the transesophageal view (not shown) in which the transducer is placed in the esophagus to orient the transducer in a position behind the heart and thereby obtain a view of the heart from that position.

After the probe 32 has been appropriately adjusted (112) the ultrasound apparatus is gated in response to the EKG wave (114) to obtain a series of frames of data between each heartbeat. For example, adjusting the frame rate between successive heartbeats as determined by the EKG wave may range in the number from approximately two to thirty frames per heartbeat.

The analog signals obtained from each gated frame are thereafter digitized (116) to obtain digitized frame signals. The digitized frame signals are thereafter recorded at 118 as framed data along with color flow information determined by the processor. Thus the information regarding the frames also includes color flow information associated with each bit or pixel which comprises the location by location information defining the frame. The data associated with each frame may be recorded in memory 74 of the image processing unit 66, or in the memory 54 of a conventional ultrasound apparatus which has been programmed to additionally operate in accordance with the present invention, or recorded in a video storage unit 60 in video format for later use on an image processing unit 66.

Thereafter, the recorded frame data and color flow information is analyzed by use of any known conventional edge detection or pattern recognition algorithm embodied in software on a computer, in order to detect (120) the edges of the moving mass of blood pool noted by the maximum color associated with the out-of-limit response. Detecting the edges of the pool of moving blood defines the outline of the pool of moving blood, as is shown in FIG. 5, where the outline 122 represents the blood pool movement under systolic conditions and the outline 124 represents the blood pool movement under diastolic conditions.

After the outline of the moving blood pool has been detected at 120, the outlines are used to calculate the various heart function results 126), or left ventricle (LV) functioning parameters, using the edge movement data.

Calculating the results at step 126, again involves the use of a number of selected different manual or automatic processes. For example, one manual analysis involves selecting from all the data frames obtained between successive heartbeats, the maximum area of the moving blood pool as determined by the edge detection at 120, and the minimum area of the moving blood pool. By determining the area of the maximum area and the minimum area, which correspond to the diastolic and systolic conditions of the heart chamber, it is possible to estimate the maximum and minimum volume of the moving blood pool in order to calculate the ejection fraction. The ejection fraction is simply the difference between the maximum and minimum volumes divided by the maximum volume. This ejection fraction can be calculated manually using the images presented at the display or can be calculated automatically by computer processor. Calculation of the maximum/minimum areas may also be accomplished as simply as counting the number of pixels within each area defined by the detected edges.

The estimation of the volume of the moving blood pool from a two-dimensional cross-sectional area involves one of several known methods. One involves the assumption that the LV is in the shape of a prolate ellipsoid. The volume of a prolate ellipsoid can be calculated from the length, height and width of the ellipsoid. A second method for estimating the volume of the moving blood pool does not rely on the assumption that the LV is in the shape of a prolate ellipsoid. Instead the volume is broken up into circular slices or cross-sections of predetermined thickness. This method, known as Simpson's Rule, allows the calculation of a irregularly shaped chamber such as when the LV has an aneurysm. The combined volume of the circular slices is equal to the volume of the LV.

To aid in these calculations it is sometimes desirable to display the information (128). In addition to the typical CRT display, the display may also take the form of plotters and printers, for example. It should be noted that the display can be effected from the information attained at any of the steps 118, 120 and 126, should the operator so desire.

In accomplishing the calculation, it is sometimes desirable to look at successive heartbeats in order to obtain the systolic and diastolic conditions. However, the number of successive heartbeats needed to calculate the desired results according to the present invention is considerably smaller than the number needed in nuclear medicine techniques or cardiographic techniques, for example.

In addition to calculating the ejection fraction, it is also possible to obtain data sufficient to analyze a large number and variety of heart functions, many of which have been extensively described in the relevant literature.

A presently preferred embodiment of the present invention has been described above with a degree of specificity. It should be understood, however, that this description has been made by way of preferred example and the invention itself, however, is defined by the scope of the appended claims.

The invention claimed is:

1. A method of ultrasonically determining changes in the size of a moving pool of blood within a moving organ of a human body, comprising:
    transmitting an ultrasonic signal into the moving blood pool and the organ in the human body;
    receiving a reflected ultrasonic signal reflected by the moving blood pool and the moving organ;
    analyzing the reflected signal to obtain movement information indicative of the movement of the pool of blood and the movement of the organ;
    separating from the movement information that information indicative of a greater rate of movement than the rate of movement of the organ; and
    determining the blood pool size changes from the movement information indicative of a greater rate of movement than the movement of the organ.

2. A method as defined in claim 1 wherein determining the blood pool size changes further comprises:
    creating an image of the blood pool from the movement image indicative of a greater rate of movement than the movement of the organ.

3. A method as defined in claim 1 further comprising:
    using the separated information to determine the size of the moving pool of blood.

4. A method as defined in claim 2 further comprising:
    selecting a range of limits for rates of movement to be used in coloring the created image, using the movement information;
    coloring the portions of the created image with a first color representative of movement in one direction and within the selected range;
    coloring the portions of the created image with a second different color representative of movement in an opposite direction of the one direction and within the selected range;
    coloring the portions of the created image with a third color representative of movement in the one and the opposite directions which is out of the selected range; and
    using the portions of the created image which are colored with the third color to determine the size of the moving pool of blood.

5. A method as defined in claim 4 further comprising:
    automatically detecting the boundaries of the portions of the created image which are colored with the third color.

6. A method as defined in claim 5 further comprising:
    automatically determining the volume of the blood pool from the boundaries of the portions of the created image which are colored with the third color.

7. A method as defined in claim 2 further comprising:
    selecting a range of limits for rates of movement to be used in coloring the created image, using the movement information;
    coloring the portions of the created image with a color representative of rates of movement which are out of the selected range; and
    using the portions of the created image which are colored to determine the size of the moving pool of blood.

8. A method as defined in claim 7, further comprising:
    selecting a range of limits for variations in the rates of movement to be used in coloring the created image, using the movement information; and
    coloring the portions of the created image with a color which represents both the rates of movement which are out of the selected range of rates and the variations in the rates of movement which are out of the selected range of variations.

9. A method as defined in claim 3 further comprising:
    determining the size of the pool of blood in a systolic condition;
    determining the size of the pool of blood in a diastolic condition; and
    evaluating the performance of the organ by comparing the determined sizes of the pools of blood in the systolic and diastolic conditions.

10. A method as defined in claim 9 further comprising:
    determining a fractional relationship defined by the difference in size of the determined sizes of the pools of blood in the systolic and diastolic conditions relative to either one of the determined size of the pool of blood in the systolic or diastolic conditions.

11. A method as defined in claim 10 wherein the organ is the heart and the fractional relationship is the ejection fraction of the left ventricle of the heart.

12. A method of imaging moving pools of blood in a human body ultrasound, comprising:
    transmitting an ultrasonic signal of a predetermined frequency into a human body;
    receiving a reflected ultrasonic signal from the human body;
    continuously sweeping the direction of the transmitted ultrasonic signal through a scan angle comprising a predetermined arc;
    comparing the reflected signal to the transmitted signal to determine a difference in frequency therebetween and an elapsed time between the time of transmission and the time of reception;
    generating a color image based upon the difference in frequency, the elapsed time and the scan angle, wherein a frequency shift in one direction is represented by a first color and a frequency shift in an opposite direction is represented by a second color; and
    determining the uncertainty of the frequency shift based upon sampling theory and representing all such uncertain received signals as a third color.

13. A method as defined in claim 12, further comprising:
    displaying said color image.

14. A method as defined in claim 12, further comprising:
    processing said color image to determine:
        the edges of regions of the third color in the image,
        a magnitude of the two-dimensional area of said regions; and
        a magnitude of the three-dimensional volume of said regions in the human body.

15. A method as defined in claim 14, further comprising:
    displaying said magnitude of the three-dimensional volume of said region on a display.

16. A method as defined in claim 14 wherein each step of the method is repeated at a subsequent time to determine the change in the magnitude of the three-dimensional volume of said region.

17. A method as defined in claim 16, further comprising:
   displaying said change in the magnitude of the three-dimensional volume.

18. An apparatus for imaging with ultrasound moving pools of fluids, having a three-dimensional volume, confined in moving tissues in a human body, comprising:
   means for transmitting a series of ultrasonic signals of a predetermined frequency into the human body;
   means responsive to the transmitted series of ultrasonic signals reflecting from each moving component of the moving tissues and fluids within the human body to create a series of electrical echo signals which correspond to each moving component and which have a frequency different from said transmitted frequency by an amount proportional to the velocity of the moving components of said tissues and fluids from which said series of transmitted signals were reflected;
   processor means responsive to the series of echo signals for:
   calculating the range, position and velocity of each component of said tissues and fluids within the human body,
   categorizing by velocity each component of said moving tissues and fluids;
   determining an area of those fluids having a velocity magnitude relatively greater than the velocity magnitude of the surrounding tissues and relatively greater than those other fluids having a velocity similar to the velocity of the surrounding tissues; and
   estimating the three-dimensional volume of the moving fluid represented by said determined area of fluid.

19. Apparatus as defined in claim 18, further comprising:
   display means connected to said processor means and operative for displaying said estimated volume.

20. Apparatus as defined in claim 19, wherein the tissue includes the heart, the fluid includes blood, and said processor means further operatively:
   performs said calculation, categorization, determination and estimation functions at a systolic and diastolic phase of a beat or cycle of the heart, and
   determines a change in the three-dimensional volume based on the three-dimensional volume estimations obtained at the systolic and diastolic phases of the heart beat.

21. An apparatus for imaging with ultrasound moving pools of fluid confined in moving tissues in a human body, comprising:
   means for transmitting a series of ultrasonic signals of a predetermined frequency into the human body;
   means responsive to the series of ultrasonic signals reflecting from the tissues and fluids within the human body to create a series of electrical echo signals which have a frequency different from said transmitted frequency by an amount proportional to the velocity of said tissues and fluids from which said series of transmitted signals were reflected;
   processor means responsive to the series of echo signals and operative for:
   calculating range, position and velocity information from the echo signals wherein the calculated range, position and velocity information describe the range, position and velocity, respectively, of said tissues and fluids within the human body,
   comparing the calculated velocity information with a predetermined limit which represents a maximum velocity to obtain out of limit velocity information which is greater than the predetermined limit and to obtain within limit velocity information which is less than the predetermined limit,
   generating a color video signal from said calculated range and position information and from the out of limit and within limit velocity information, the color video signal describing the out of limit velocity information by a first color and the within limit velocity information by at least one different second color, and
   adjusting the predetermined limit to identify by the first color those fluids having a velocity with a magnitude relatively greater than the velocity of the surrounding tissues and relatively greater than those fluids having a velocity similar to the velocity of the tissues and to identify by the second color those tissues and fluids having a velocity similar to the velocity of the tissues.

22. Apparatus as defined in claim 21, further comprising:
   display means connected to said processor means and receptive of said color video signal and operative for displaying a color image based on said color video signal, the color image displayed presenting those areas of the image representative of the fluid velocity movement which is greater than the adjusted predetermined limit.

* * * * *